United States Patent [19]

Urquhart et al.

[11] Patent Number: 4,493,702
[45] Date of Patent: * Jan. 15, 1985

[54] PARENTERAL ADMINISTRATION USING OSMOTICALLY MOTIVATED DELIVERY SYSTEM

[75] Inventors: John Urquhart, Palo Alto; Felix Theeuwes, Los Altos, both of Calif.

[73] Assignee: ALZA Corporation, Palo Alto, Calif.

[*] Notice: The portion of the term of this patent subsequent to Feb. 21, 2001 has been disclaimed.

[21] Appl. No.: 542,466

[22] Filed: Oct. 17, 1983

Related U.S. Application Data

[63] Continuation of Ser. No. 325,206, Nov. 27, 1981, Pat. No. 4,432,756.

[51] Int. Cl.$^3$ .............................................. A61M 5/00
[52] U.S. Cl. ........................................ 604/80; 604/85; 604/246
[58] Field of Search ................................ 604/80, 83–85, 604/56, 92, 246

[56] References Cited

U.S. PATENT DOCUMENTS

| | | | |
|---|---|---|---|
| 3,305,446 | 2/1967 | Bechtol et al. | 167/22 |
| 3,756,237 | 9/1973 | Chittenden et al. | |
| 3,760,984 | 9/1973 | Theeuwes | 222/95 |
| 3,797,494 | 3/1974 | Zaffaroni | |
| 3,845,770 | 11/1974 | Theeuwes | |
| 3,854,480 | 12/1974 | Zaffaroni | |
| 3,921,636 | 11/1975 | Zaffaroni | |
| 3,941,126 | 3/1976 | Dietrich et al. | |
| 3,948,254 | 4/1976 | Zaffaroni | |
| 3,993,072 | 11/1976 | Zaffaroni | |
| 3,993,073 | 11/1976 | Zaffaroni | |
| 3,995,631 | 12/1976 | Higuchi et al. | |
| 4,177,256 | 12/1979 | Michaels et al. | 424/22 |
| 4,217,894 | 8/1980 | Franetzki | |
| 4,219,022 | 8/1980 | Genese | |
| 4,233,973 | 11/1980 | Shukla | |
| 4,256,104 | 3/1981 | Muetterties | |

FOREIGN PATENT DOCUMENTS 497181 11/1970 Switzerland .

OTHER PUBLICATIONS

Surgery, vol. 70, pp. 674–677, 1971, Ferenchak, et al., "Drop Size and Rate in Parenteral Infusion".
Brit. J. Anaesth., vol. 43, pp. 681–686, 1971, "Latta—Pioneer in Saline Infusion".
Amer. J. Hosp. Pharm., vol. 32, pp. 892–897, 1975, Paxinos, et al., "Combined Volume Control Set–Piggyback System for Intermittent Intravenous Therapy".

Primary Examiner—Stephen C. Pellegrino
Attorney, Agent, or Firm—Paul L. Sabatine; Edward L. Mandell; Steven F. Stone

[57] ABSTRACT

A parenteral delivery set is disclosed for administering a beneficial agent to a recipient. The set comprises (a) a primary container of a medical fluid; (b) a primary tubing in fluid communication with the primary container; (c) a secondary container of a medical fluid; (d) a secondary tubing in fluid communication with the secondary container; (e) a formulation chamber connected to the secondary tubing and housing an agent dispensing device or the beneficial agent; and (f) a common tubing in communication with the primary tubing and the secondary tubing for communicating the set to the recipient.

3 Claims, 13 Drawing Figures

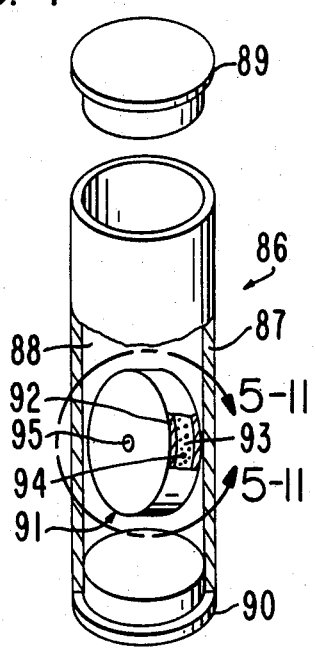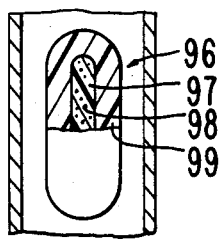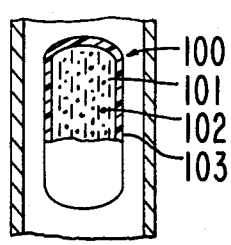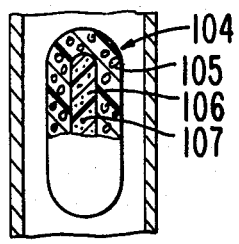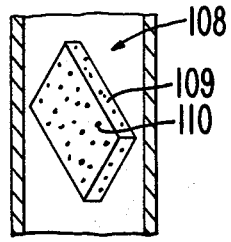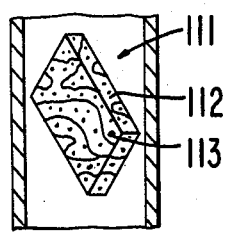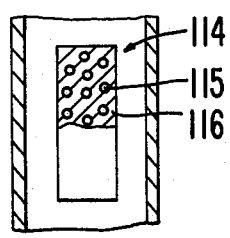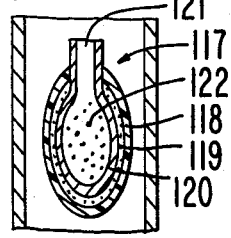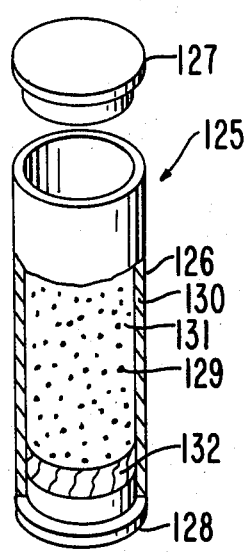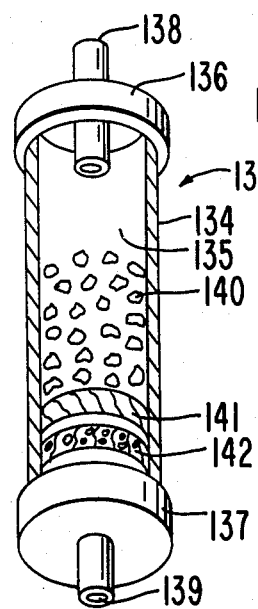

PARENTERAL ADMINISTRATION USING OSMOTICALLY MOTIVATED DELIVERY SYSTEM

CROSS-REFERENCE TO COPENDING APPLICATIONS

This application is copending with U.S. patent application filed as Ser. No. 325,204 on Nov. 27, 1981 and issued as U.S. Pat. No. 4,424,056 on Jan. 3, 1984. This application and the copending application are assigned to the ALZA Corporation of Palo Alto, Calif. This application is a continuation of U.S. patent application Ser. No. 06/325,206 filed on Nov. 27, 1981 issued as U.S. Pat. No. 4,432,756 on Feb. 21, 1984.

FIELD OF THE INVENTION

This invention pertains to a parenteral delivery system. The system comprises a primary path and a secondary path comprising a formulation chamber containing (1) an agent delivery device, or (2) a beneficial agent. The invention relates also to a method of administering parenterally an agent using the parenteral delivery system.

BACKGROUND OF THE INVENTION

The parenteral administration of sterile fluids is an established clinical practice, and the practice is used extensively as an integral part of the daily treatment of medical and surgical patients. The fluids administered parenterally, usually intravenously, include aqueous solutions of dextrose, sodium chloride, and various other electrolytes. Always administered intravenously are blood and blood substitutes. Generally, the fluids are administered from a container that is suspended above a patient, with the fluid flowing from the container through an administration set and thence to a cannula or a hypodermic needle placed in a blood vessel, usually a vein of the patient. For intraperitoneal administration of fluids, the administration set is connected to a cannula traversing the abdominal wall of the patient.

The administration of fluids parenterally is a valuable and important component of patient care. The use of parenteral fluids moreover has in recent years expanded beyond its original role of fluid and electrolyte replacement to include serving as the vehicle for the parenteral administration of beneficial agents, notably for those where it is desirable to administer by infusion via the intravenous, intra-arterial, intrapertioneal or subcutaneous routes. For example, presently a beneficial agent, such as a drug, is administered intravenously by one of the following procedures: temporarily halting the flow of medical fluid and intravenously administering a solution of the drug to the patient through an injection port in the administration set, followed by resumption of medical fluid into the patient; a drug is added to the fluid in the container, or into a volume control chamber in series with the administration set, and then carried by the flow of fluid into the patient; a drug is introduced into a so-called "piggyback" container, which is subsequently connected via a connector, in tributary fashion, to the primary administration set through which fluid is administered to the patient; or a drug is administered by a pump which, by one of various recognized pumping actions, establishes flow and this determines the flow of fluid containing the drug into a flow path entering the patient, for example, an indwelling venous catheter.

While these techniques are widely used, they have certain inherent disadvantages. For example, the administration of a drug through repeated injections into the administration set is inconvenient and represents each time a potential break in sterility; the use of pumps is expensive and sometimes inconvenient because of their size and weight; the rate of drug delivery to the patient is dependent on the flow of fluid with all currently practiced means of drug infusion; because of the relative chemical instability of aqueous solutions of many parenteral drugs, these procedures often require solubilization of the drug medication by the hospital pharmacist or by the nurse at a time proximate to its administration; and, while it is current practice to give some drugs by brief infusions, typically of 30 to 120 minutes duration repeated 3 or 4 times a day, they do not provide a means for (a) careful coordination of the procedures for solubilization and administration, (b) careful regulation of the flow of drug solution during each period of infusion to insure that infusion is completed within the recommended time, and (c) for doses prepared in advance and administered at a preselected time.

In view of this presentation, it is immediately apparent a critical need exists for a dependable and practicable parenteral therapeutic delivery system that overcomes the disadvantages associated with the systems known to the prior art. It is also apparent that a pressing need exists for a parenteral delivery system that can be used clinically for administering parenterally a beneficial agent at a controlled rate and in a beneficially effective amount to a patient according to a preselected program comprising continuous administration, repeated administration, administration at specified intervals, or as needed administration.

DISCLOSURE OF THE INVENTION

Accordingly, a principle object of this invention is to provide both a novel and useful parenteral delivery system for administering a fluid and a beneficial agent at a controlled rate and according to a chosen regimen of administration and in an improved manner for optimizing the care of a warm-blooded animal whose prognosis benefits from parenteral administration.

Another object of the invention is to provide a parenteral delivery system comprising (1) a primary fluid path, and (2) a secondary fluid path comprising a formulation chamber containing (a) an agent delivery device for delivering an agent into a medical fluid that flows into the chamber, or (b) a beneficial agent, which agent in either instance forms in situ an agent solution for administration to an animal, including a human patient.

Another object of this invention is to provide a delivery system comprising (1) a primary fluid path and (2) a secondary fluid path having a formulation chamber, and which system can be used for improved health care by making available to the practitioner (a) a mechanism for administering a fluid via the primary path, (b) a mechanism for administering a fluid containing a beneficial agent via the secondary path, and (c) a mechanism for controlling the volume and the concentration of agent administered by adjusting the rate of flow through the primary path and by adjusting concomitantly the rate of flow through the secondary path prior to their mixing into a single fluid for its subsequent administration.

Another object of this invention is to provide a parenteral delivery system that comprises a means for automatically constituting an agent formulation in situ by dissolving a given amount of agent in a given volume of fluid that can be administered at any selected time, including intermittent intravenous therapy.

Another object of this invention is to provide a parenteral delivery system that makes attainable a program of agent administration adapted to a specific need by furnishing an agent formulation comprising a known volume of fluid containing from a trace to a saturating amount of a beneficial agent that can be administered at any chosen time.

Another object of this invention is to provide a parenteral delivery system that makes possible a means for converting a continuously functioning process of agent formulation and release into a method of agent administration that occurs at predetermined periods according to a specified rate and duration of agent administration.

Another object of this invention is to provide a parenteral delivery system that makes available a regimen of agent administration comprising intervals of agent administration at a specified rate and for a specified duration, alternating with intervals during which no agent is delivered by the system.

This invention concerns a parenteral delivery system for the administration of a medical fluid containing a beneficial agent to an animal, including a human patient. The system comprises: (1) a primary fluid path consisting of a container of medical fluid and a primary tube that communicates from the container to a common tube that leads to an infusion site in the animal; (2) a secondary fluid path consisting of a minicontainer of a medical fluid in fluid communication with an agent formulation chamber. The formulation chamber comprises: (a) a wall surrounding a lumen and has a surface that permits communication with the secondary path to let a fluid flow from the container into the formulation chamber; (b) a delivery device containing a beneficial agent that is released into the formulation chamber, or a beneficial agent in the formulation chamber, which agent in either instance forms an agent formulation with fluid that enters the formulation chamber; and (c) an outlet surface that lets agent formulation leave the formulation chamber and enter the secondary path and then into the common path for administration to the patient. The system additionally comprises a mechanism that can optionally be used for converting a continuously functioning process of agent formulation and releasing into (d) the common flow path so that agent administration into the patient occurs during quantitatively predetermined intervals according to a specified rate and duration of agent infusion, or (e) from the formulation chamber into a regimen of agent administration to the patient characterized by intervals of agent infusion at a specified rate and specified duration alternating with intervals during which no agent reaches the infusion site in the patient.

BRIEF DESCRIPTION OF THE DRAWINGS

In the drawings, which are not drawn to scale but are set forth to illustrate various embodiments of the invention, the Figures are as follows:

FIG. 4 is a view of an agent formulation chamber adapted for use in the parenteral delivery system, with the chamber housing an osmotic agent delivery device;

FIG. 5 is a view of an agent delivery device comprising a release rate controlling membrane surrounding a reservoir containing a beneficial agent which device is adapted for use in an agent formulation chamber;

FIG. 6 is a view of a delivery device comprising a release rate controlling membrane surrounding a different reservoir containing a beneficial agent which device is designed for use in an agent formulation chamber;

FIG. 7 is a view of an agent delivery device comprising a microporous membrane surrounding a reservoir containing a beneficial agent which device can be used for the purpose of the invention in the formulation chamber;

FIG. 8 is a view of a delivery device comprising a matrix containing a beneficial agent which device can be used in the formulation chamber;

FIG. 9 is a view of a delivery device comprising a microporous matrix containing an agent which device can be used in the formulation chamber for carrying out the invention;

FIG. 10 is a view of a delivery device comprising depots of agent which device can be used in the formulation chamber;

FIG. 11 is a view of a delivery device comprising a housing and a driving member surrounding a flexible container that can be used in a formulation chamber;

FIG. 12 is an opened view of a formulation chamber comprising a beneficial agent and a release rate controlling membrane; and, FIG. 13 is an opened view of an agent formulation chamber comprising a beneficial agent, a release rate controlling membrane and a filter.

In the specification and the drawings, like parts in related Figures are identified by like numbers. The terms appearing earlier in the specification and in the description of the drawings are described hereafter in the disclosure.

MODES FOR CARRYING OUT THE INVENTION

Figure 1:
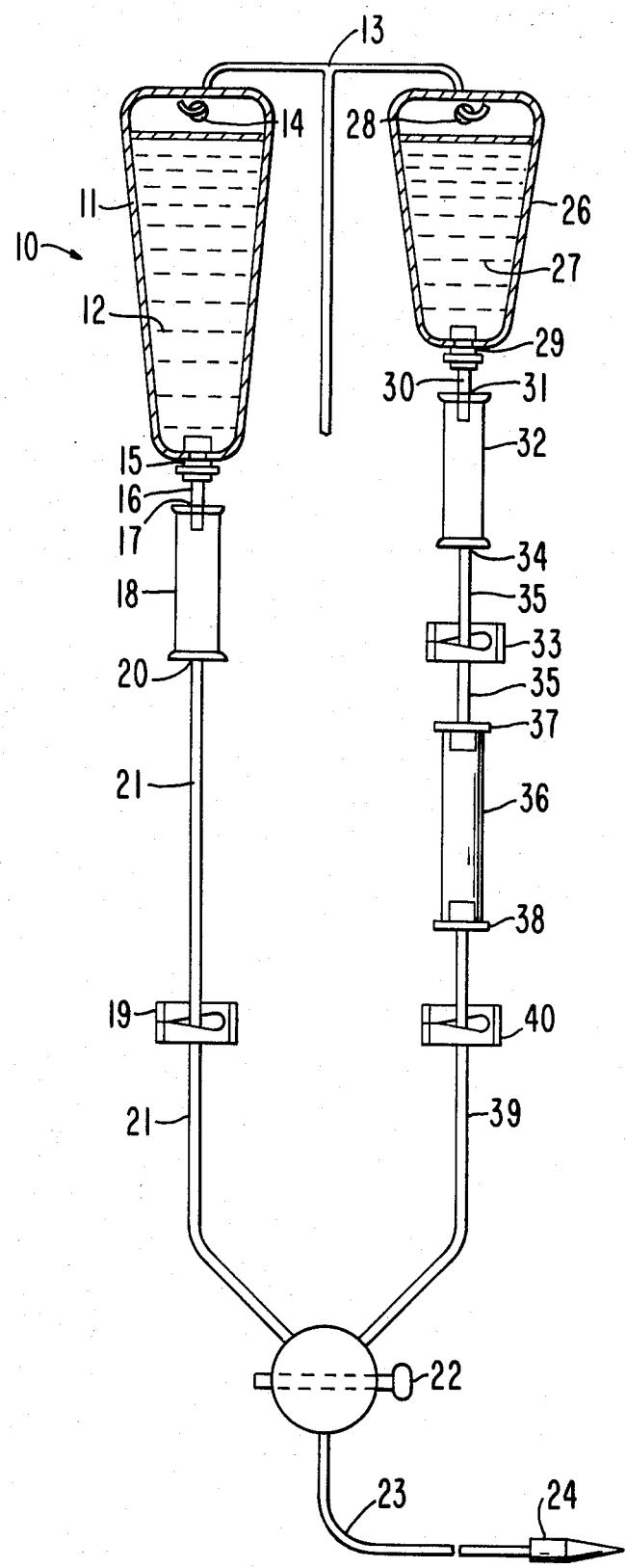
FIG. 1 is a perspective view of a parenteral delivery system provided by the invention.

FIG. 1 represents a parenteral delivery system provided by the invention and designated by the numeral 10. System 10 comprises a primary container 11 formed of a flexible, or a semi-rigid preferably transparent plastic, such as a non-toxic polyolefin, polyvinyl chloride or the like. Primary container 11 is a large volume parenteral, LVP, container and it contains a medical fluid 12 adapted for parenteral, intravenous or other therapy. Medical liquid 12 in container 11 will be typically a sterile solution, such as an aqueous solution of dextrose, electrolytes, or saline. Container 11, in the embodiment illustrated, is non-vented, the medical fluid is at atmospheric pressure, and the container collapses as it empties of medical fluid 12. Container 11 usually is adapted to be hung neck-down from a hanger 13 by a bib or hole 14 that connects, or is integrally formed as part of container 11. Container 11, at its end distant from its hanging end, that is, at its neck end, has an administration port adapted for receiving a primary fluid path.

The primary path is used to deliver medical fluid 12 by parenteral therapeutic system 10 to a patient. The primary path is sterile, pyrogen-free, and disposable. The primary path comprises the components described hereinafter, and it connects with port 15 of container 11. Port 15 can be a diaphragm in container 11, now shown, or port 15 can be an adapter for receiving a hollow connector 16. Connector 16 is made to receive end 17 of drip chamber 18. Drip chamber 18 is used to trap air and it also permits, in cooperation with regulator clamp 19, adjustment of the rate of flow of medical fluid 12 from container 11 as the flow proceeds dropwise. An outlet 20 of drip chamber 18 is connected to one end of a primary tube 21 that passes through regulator clamp 19 for pinching its internal diameter to regulate flow in cooperation with drip sight chamber 18. The other end of primary tube 21 connects to a valve 22, beyond which common tube 23 connects from valve 22 to an adapter needle assembly 24 that is inserted, for example, into the vein of a warm-blooded animal.

System 11 further comprises a secondary fluid path, which secondary path consists of a secondary container 26 or minibag formed of a flexible, or a semi-rigid preferably transparent plastic, such as a non-toxic polyolefin, polyvinyl chloride or the like. Secondary container 26 is a small volume parenteral, SVP, container and it contains a medical fluid 27 adapted for parenteral, intravenous or other therapy. Medical fluid 27 is a pharmaceutical vehicle for parenteral administration, that is, it is a pharmaceutical carrier for a drug that is to be administered to a recipient. Container 26, in the embodiment illustrated, is non-vented, medical fluid 27 is at atmospheric pressure, and the container collapses as it empties of medical fluid 27. Container 26 is adapted to be hung neck-down from a hanger 13 by a bib or hole 28 that connects, or is integrally formed as a part of container 26. Container 26, at its end distant from its hanging end, that is, at its neck end, has an administration port adapted for receiving a secondary fluid path.

The secondary fluid path provided by the invention is used to deliver medical fluid 27 to which a drug is added to a patient. The secondary path is sterile, pyrogen-free and disposable. The secondary path comprises the components describer hereinafter; and it connects with port 29 of container 26. Port 29 can be a diaphragm in container 26, not shown, or port 29 can be an adapter for receiving a hollow connector 30. Connector 30 is made to receive end 31 of drip chamber 32. Drip chamber 32 is used to trap air and it also permits, in cooperation with regulator clamp 33, adjustment of the rate of flow of medical fluid 27 from container 26 as the flow proceeds dropwise. An outlet 34 of drip chamber 32 is connected to one end of a segment of secondary tube 35 passing through regulator clamp 33 for pinching its internal diameter to regulate flow in cooperation with sight drip chamber 32. The other end of secondary tube 35 connects to an agent formulation chamber 36. Regulator clamp 33 is used for governing the flow of fluid into an agent formulation chamber 36. Formulation chamber 36 is made of glass or plastic, and it is preferably transparent. Formulation chamber 36 can have any shape adapted for use in a parenteral therapeutic system, and it is preferably round and its length exceeds its width. The end of secondary tube 35 mates snugly with end cap 37 of chamber 36. The end of the secondary tube can fit into cap 37 or it can slide over a tube receiving member of cap 37 to form an air-tight, leak-proof chamber for containing at least one beneficial agent, or a delivery device. Chamber 36 optionally is equipped with a release rate controlling membrane, not shown in FIG. 1, for example a microporous membrane or the like, that governs the rate of release of agent solution from chamber 36. A release rate controlling membrane can rest on a sintered glass support integrally made into the chamber, optionally a membrane can be sealed adhesively to the inside wall of chamber 36, fused thereto, be supported by the wall of the chamber pinched inwardly, rest on a rim in the chamber, or it can be supported or suitably fixed to end cap 38 positioned in chamber 36. A segment of secondary tube 39 conveys agent solution from chamber 36 to valve 22. A regulator clamp 40 is provided on tube 39 as an aid in governing the flow of agent solution from the formulation chamber. Regulator clamps 40 can be used alone, in cooperation with clamp 33, in cooperation with valve 22, and both in cooperation with valve 22 for governing fluid flow and agent solution flow through the secondary path. Valve 22, in a presently preferred embodiment, is a two position valve. Agent solution is conveyed from valve 22 through common tube 23 to needle assembly 24 for administration to a recipient.

In operation, valve 22 in one position permits the passage of a drug solution from chamber 36 to flow into common tube 23, while concomitantly stopping flow via tube 21; in its alternate second position, valve 22 stops flow of fluid in tubes 35 and 39, but it allows flow in tube 21. When valve 22 is in its first position, the flow of medical fluid reaches the patient at a rate determined by the setting of regulating clamp 33 with clamp 40 opened to flow; when valve 22 is in its second position, the flow of medical fluid reaches the patient at a rate determined by the setting of flow regulating clamp 19. During the intervals of time valve 22 is in its second position, drug formulation proceeds in the presence of fluid in chamber 36 and its release continues from formulation chamber 36 into tube 39, but it cannot reach the patient, and so it accumulates in chamber 36 and tube 39. When valve 22 is switched to its first position, accumulated drug formulation solution in chamber 36 and tube 39 enters the patient, the quantity of which is governed by the following pharmacodynamic expression:

$$\int_{t_j}^{t_k} R_1(t)dt + \int_{t}^{t_L} R_2(t)dt$$

wherein $t_j$ equals the time valve 22 is switched from position 1 to position 2; $t_k$ equals the time valve 22 is switched from position 2 to position 1; $t_L$ equals the time valve 22 can be switched from position 1 back to position 2; and $R_1(t)$ equals the rate at which formulation chamber 36 prepares and releases drug in solution; $R_2(t)$ is the rate at which the formulation chamber prepares drug solution during free flow of intravenous fluid. The rate at which agent reaches a patient when valve 22 is switched to position 1, is related to the flow regulation imposed by clamp 33 which preferably should be adjusted to allow flow to occur at a rate which insures that all accumulated agent enters the patient. While the above system and its operation were described with a representative manually operated valve, it is to be understood other valve systems are embraced by this invention. For example, electro-mechanical devices that automatically switch back and forth between positions 1 and 2 at preset time intervals are within the scope of this invention.

Figure 2:
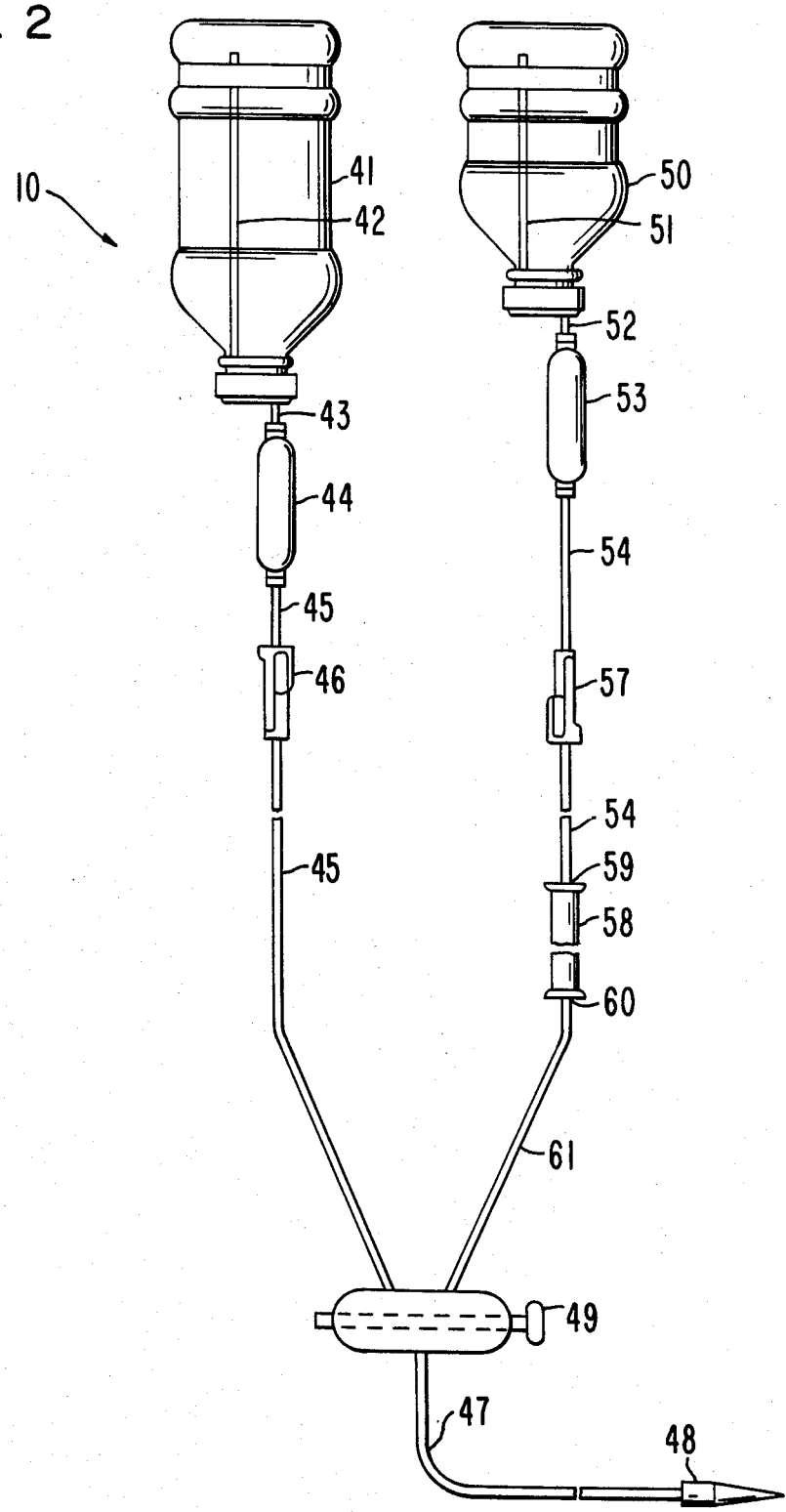
FIG. 2 is a view illustrating another embodiment of the parenteral delivery system.

FIG. 2 illustrates another intravenous system 10 provided by the invention. System 10 comprises a primary path having in combination a container 41 that is a reservoir of a pharmaceutically acceptable liquid and it has an internal venting tube 42 which allows air to enter container 41 as medical fluid is infused into a patient. Container 41 is a large volume parenteral of a sterile fluid intended for the modification and maintenance of physiological functions in a recipient. Container 41 is closed with a stopper, not shown, and it has a hole for venting tube 42. Container 41 is connected through a non-vented hollow spike adaptor 43 to a primary delivery path for sending medical fluid from container 41 through the path to a patient. Spike 43 is in fluid communication with a drip chamber 44, which as previously described, is made preferably of a see through material, such as a glass or plastic for visibly counting the number of drops that pass through said drip chamber over unit time. Medical fluid leaves drip chamber 44 through a section of a primary tube 45 that passes through a flow regulator clamp 46, that is used for regulating fluid flow from container 41, and for conveying fluid through tube 45 to two-way valve 49, and hence from valve 49 through fluid communicating common tube 47 and needle assembly 48 to a recipient.

System 10 of FIG. 2 also comprises a secondary path consisting of container 50 that is a means for storing a pharmaceutically acceptable liquid. Container 50 has an internal venting tube 51 for letting air enter container 50 as liquid leaves the container. Container 50 is a minicontainer or a minibottle and it holds about 100 to 250 milliliters of liquid that is used for continuous drug transport, or for intermittent drug transport to a recipient. Container 50 is closed with a stopper, not shown, and it has a hole for venting tube 51. Container 50 is connected through a non-vented hollow spike adaptor 52 to a secondary delivery system for sending medical liquid from container 50 containing a drug through the secondary path to a patient. Spike 52 is in fluid communication with a drip chamber 53 designed for counting the number of drops that pass through said drip chamber over time. Medical fluid leaves drip chamber 53 through a section of secondary tube 54 that passes through a flow regulator valve 57 that is used for regulating liquid flow from container 51. Secondary tube 54 passes through clamp 57 and it can be used as an on-off, or a volume flow regulator for admitting fluid into an agent formulation chamber 58. Agent formulation chamber 58 is as described earlier comprised of a wall formed of a fluid impermeable material that surrounds an internal space for housing a dosage unit amount of a beneficial agent, or a delivery device. Chamber 58 has a known volume and preferably a volumetric scale thereon for indicating the volume of fluid in said chamber. Chamber 58 has an end 59 adapted for receiving incoming tube 54 and fluid from container 50, and it has an end 60 adapted for receiving outgoing tube 61. Tube 61 conveys fluid carrying the beneficial agent from chamber 58 to valve 49, and thence through fluid communicating common tube 47 to needle assembly 48, and to the recipient.

In operation, parenteral delivery system 10 of FIG. 2 is used like parenteral delivery system 10 of FIG. 1. That is, system 10 of FIG. 2 can be used (1) for administering a medical fluid that is free of agent by closing regulator 57, opening regulator 46 and positioning valve 49 to let fluid flow from tube 45 and into tube 47; (2) for administering continuously a medical fluid containing a beneficial agent by closing regulator 46, opening regulator 57 to permit fluid to flow through formulation chamber 58 wherein the agent is added to the fluid, and positioning valve 49 to let fluid flow through tube 61 and into tube 47; and (3) for administering at a selected dosing time a given volume of fluid containing a known amount of agent by (a) permitting fluid to flow through the secondary path while setting valve 49 in closed position for the secondary path, (b) permitting a known volume of fluid to enter the formulation chamber, which volume is ascertained by reading the meniscus against the volumetric scale on the chamber, and closing regulator clamp 57 to stop the flow of additional fluid into the formulation chamber, (c) formulating the agent formulation in the chamber by dissolving a given amount of agent present in the chamber, or delivered by a device therein, in the known volume of fluid, which amount of agent solubility in the fluid dissolved over time, and (d) dosing a recipient with the agent solution whenever desired by positioning valve 49 to let it flow from the formulation chamber.

Figure 3:
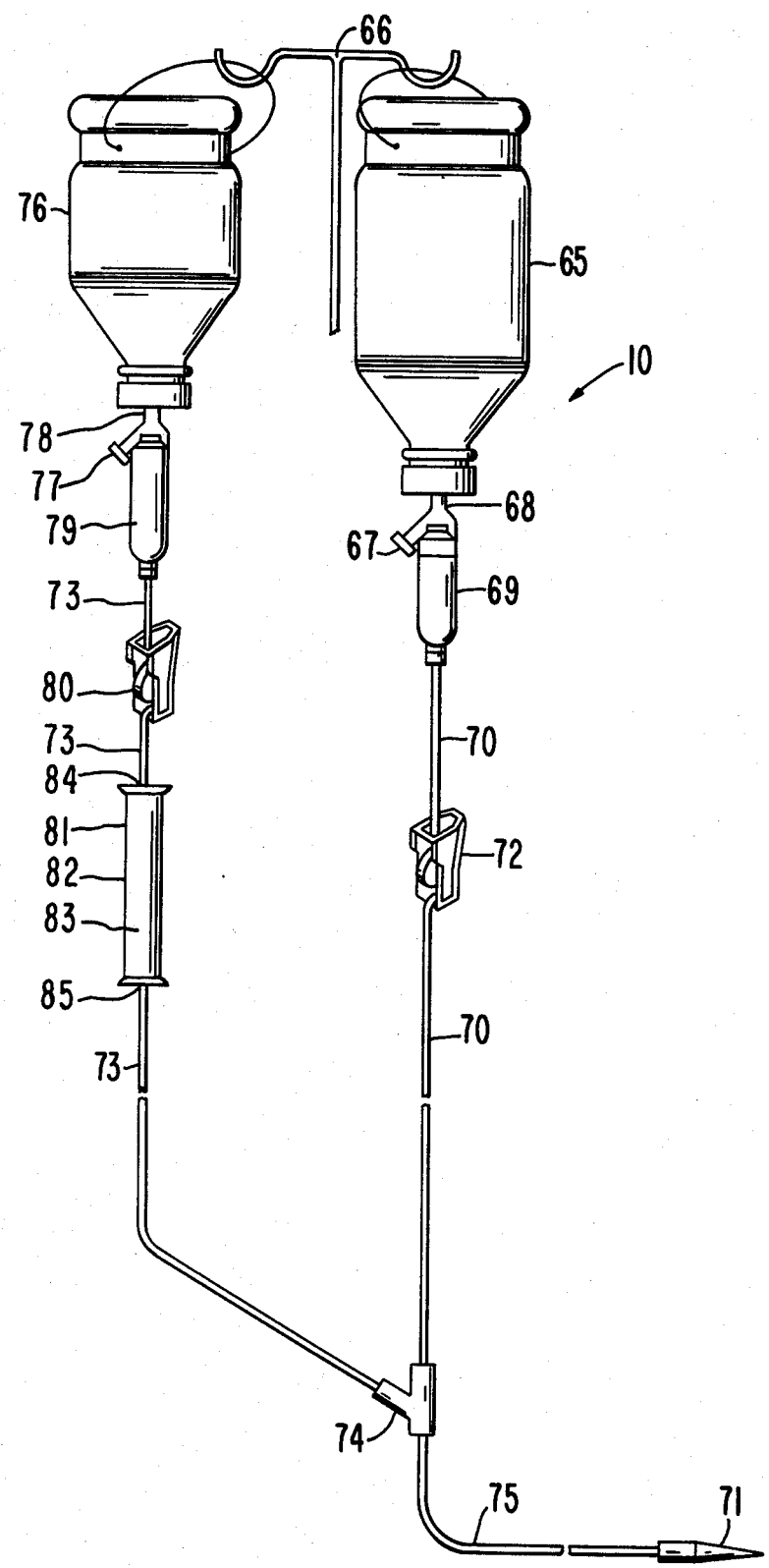
FIG. 3 is a view of yet another embodiment of the parenteral delivery system.

FIG. 3 represents a parenteral delivery system provided by the invention and designated by the numeral 10. System 10 of FIG. 3 illustrates a vented-type system that requires air to operate. System 10 comprises a glass container 65, suitably sealed with a rubber stopper and it contains a medical fluid acceptable for parenteral including intravenous administration. Container 65 is supported in delivery position by support 66, and air enters container 65 via air filter 67 connected to container 65 through spike 68 that is hollow and pierces the rubber closure of container 65. The other point of spike 68, not seen, enters a drip chamber 69 and it conveys medical fluid from container 65 into drip chamber 69. Drip chamber 69 is connected to a primary fluid path 70 formed of a medical grade tubing that conveys medical fluid to needle 71. A roller valve clamp 72 is provided on fluid path 70 for restricting the internal diameter of primary path 70 for regulating the flow of fluid through primary path 70. System 10 of FIG. 3 also comprises a secondary fluid path 73 that joins a common path 75 at branch coupler 74. Branch coupler 74 can be made as a Y-type connecting tube for receiving primary path 70, secondary path 73 and common path 75.

The secondary path comprises a container 76 that is a minicontainer or a minibottle formed of glass, and suitably sealed with a rubber stopper, not visible, and it contains a medical fluid acceptable for parenteral including intravenous administration. Container 76 is supported in delivery position by support 66, and air enters container 76 through a filter 77 connected to container 76 through spike 78, which spike is hollow and pierces the rubber closure of container 76. The other point of spike 78, not seen, enters a drip chamber 79 and it conveys medical fluid from container 76 into drip chamber 79. Drip chamber 79 is connected to a secondary fluid path 73 formed of a medical grade tubing that conveys medical fluid transporting a beneficial agent to needle 71. A roller valve clamp 80 is provided on secondary fluid path 73 for restricting the internal diameter of secondary path 73 for regulating the flow of fluid through the secondary path into agent formulation chamber 81. Agent formulation chamber 81 is sized and adapted for use in parenteral delivery system 10. Agent formulation chamber 81 is self-contained, self-priming, self-powered and amenable to low cost manufacture. Formulation chamber 81 is lightweight and disposable and it comprises a wall 82 that surrounds and defines an internal lumen or space 83. Formulation chamber 81 has an inlet 84 for receiving secondary path 73 and it has an outlet 85 also adapted for placing chamber 81 in secondary path 73. Chamber 81 is made of glass, plastic or the like, and as illustrated it is made of a transparent material for viewing its structure. Chamber 81 can house a beneficial agent or an agent delivery device. An agent formulation formed in chamber 81 leaves chamber 81 through secondary path 73, couple 74 and into common path 75 for infusion into a recipient.

The agent in formulation chamber 81 can be in any pharmaceutical state that forms an agent formulation with a medical fluid that enters chamber 81, and the use of chamber 81 with an agent therein does not require any reconstitution, or admixture prior to use. An agent formulation formed in chamber 81 leaves the chamber through secondary path 73 and it enters common path 75 for administration to an animal, including a human patient, through needle 71. Exemplary pharmaceutically acceptable forms that can be used in chamber 81 include solid, crystalline, microcrystalline, particle, pellet, granules, powder, tablet, spray-dried, lypohilized, forms that dissolve or undergo disintegration and dissolution in the presence of a parenteral fluid including intravenous fluids, compressed forms that undergo disintegration and dissolution in the presence of a fluid such as compressed, compressed powders, compressed granules, friable layers of agent, and/or the like. Agent formulation chamber 81 generally will store an amount of agent for executing a prescribed therapeutic or beneficial program. That is, an amount of agent for the pre-programmed, delivery of a therapeutically or a beneficially effective amount of the agent to produce a therapeutic or a beneficial result. Agent formulation chamber 81 generally will have a capacity of from about 10 milliliters to 250 milliliters of fluid or more, and it can house from about 5 milligrams to 20 grams of agent or more. The expression beneficial agent, as used herein, generically denotes any substance that produces a therapeutic or a beneficial result, such as a drug, a carbohydrate, an electrolyte and/or the like. The term fluid or liquid denotes a fluid, or a liquid that can be administered parenterally including intravenously, comprising pharmaceutically acceptable fluids that are also a pharmaceutically acceptable carrier for an agent, such as water, isotonic saline, Ringer's lactate, and the like. The term formulation, and agent formulation as presently used herein, generically indicates the beneficial agent is formulated, mixed, added, dissolved, suspended, solubilized, formulated into a solution, carried and/or the like in or by the fluid in a physical-chemical form acceptable for parenteral including intravenous administration. The flow of medical fluid into formulation chamber 81 can be started, stopped or regulated by clamp 80 that permits tube 73 to remain opened, shut or partially obstructs the passage of fluid through tube 73, and correspondingly the flow of agent solution likewise can be governed from chamber 81.

The delivery device housed in formulation chamber 81 releases an agent at a rate controlled by the device. The agent, on its release, is formulated in the chamber with fluid that is a pharmaceutically acceptable carrier for the agent into a parenteral including intravenous administrable agent formulation, such as a drug solution. Devices that can be used for this purpose are those that release an agent by dissolution, diffusion or osmotic mechanism, or by other physical-chemical mechanism that produces an agent formulation. The amount of agent in a formulation made in chamber 81 can be a trace amount to a saturating amount. The delivery devices, in one presently preferred embodiment are devices that cease releasing agent or shut themselves off in the presence of a saturated agent formulation, that is a saturated solution.

In operation, parenteral delivery system 10 as illustrated in FIG. 3 can be used by a physician, a nurse, or a practitioner in a hospital setting as follows: (1) for administering a medical fluid by adjusting regulator valve 80 to prevent the flow of fluid into formulation chamber 81, thus assuring that fluid will flow through primary path 70 and into skin piercing means 71; (2) for administering a medical fluid containing a beneficial agent by adjusting regulator valve 72 to prevent the flow of fluid through primary path 70, thereby directing the flow of fluid from secondary path 73 through opened valve 80 and into formulation chamber 81, with agent formulation leaving chamber 81 through tube 73, union 74, tube 75 and into skin piercing means 71; and (3) for administering an amount of agent in a known volume of fluid arrived at by regulating fluid flow through valve 72 and regulating fluid flow through valve 80 and its accompanying flow through chamber 81, which fluid in both instances mixes into a common fluid at coupling 74 for its subsequent administration to a recipient. The operations provided by this embodiment of the invention makes available continuous and interrupted agent administration, and intervals of agent-free fluid administration.

The performance of a parenteral delivery system used for the purpose of the invention, also can be described mathematically in terms of the physical and chemical functionality of the parenteral system. Generally, parenteral systems encompassed by this invention are those for which $Q_R \leq 0.1 Q_{KVO}$, wherein $Q_{KVO}$ is the flow of fluid required to maintain flow into the veins of an animal in which the flow path terminates, by needle or catheter. This flow is referred to as the "keep vein open", rate $Q_{KVO}$, and it typically is for an adult patient about 10-20 drops per minute, or 0.5-1.0 ml per minute. The symbol $Q_R$ is the maximum rate of fluid flow needed for the parenteral delivery system to deliver a solution at its label rate. Thus, parenteral systems for adult use require less than 0.05-0.1 ml/min to achieve label delivery rate, and show independence of delivery rate from flow at all higher flows are encompassed by this invention. Delivery systems for pediatric use will have a lower absolute limit, but still satisfy the general criterion $Q_R \leq 0.1 Q_{KVO}$.

FIG. 4 depicts a formulation chamber 86 housing a delivery device that can be used in the secondary path of the parenteral delivery system of FIGS. 1 to 3. The formulation chambers described in this specification are the invention disclosed and claimed by Felix Theeuwes in copending patent applications Ser. No. 06/310,047 filed on Oct. 9, 1981 and Ser. No. 06/312,491 filed on Oct. 19, 1981. Both of these applications are assigned to the ALZA Corporation of Palo Alto, Calif., the assignee of this patent application.

FIG. 4 depicts formulation chamber 86, housing a delivery device. The Figure is enlarged for illustrating its components. Turning to FIG. 4 in detail, chamber 86 is seen comprising a wall 87 that has a section removed for viewing its internal space 88. Chamber 86 has an inlet 89 adapted and sized for placing chamber 86 into the secondary path of a parenteral therapy system, and it has an outlet 90 also adapted and sized for placing chamber 86 in the system. Inlet 89 and outlet 90 can be optionally a female for receiving a tube, not shown, a rubber closure that can be pierced by a needle attached to an incoming and outgoing tube, or any other suitable means adapted for placing chamber 86 in a parenteral system. In chamber 86 of FIG. 4, the chamber is seen comprising a pair of caps that constitute inlet 89 and outlet 90. The caps fit into the chamber and they are made of self-sealing rubber through which a needle or a hollow spike can be inserted, or of rubber with a pre-drilled hole covered by a latex disc through which the secondary path can be inserted for establishing fluid communication with the inside 88 of chamber 86. The delivery device 91 illustrated in FIG. 4 is an osmotic rate-controlled solid dosage delivery form as described by patentee Felix Theeuwes and Takeru Higuchi in U.S. Pat. No. 3,845,770. The osmotic device 91 seen in opened section comprises a semipermeable wall 92, such as cellulose acylate, cellulose diacylate, cellulose triacylate, cellulose acetate, cellulose diacetate, cellulose triacetate, that surrounds and forms an agent or drug compartment 93. Compartment 93 contains an agent formulation 94, represented by dots, which formulation exhibits an osmotic pressure gradient across wall 92 of device 91 against fluid in chamber 86. The agent formulation can comprise an agent that exhibits an osmotic pressure gradient, or the agent formulation can comprise an agent mixed with an osmotically effective solute, such as sodium chloride, potassium chloride and the like, that exhibit an osmotic pressure gradient substantially greater than the fluid in chamber 86. A passageway 95 extends through semipermeable wall 92 and communicates with compartment 93 and the exterior of device 91. In operation, fluid enters into chamber 86 and is imbibed through the semipermeable wall of device 92 into compartment 93 in a tendency towards osmotic equilibrium at a rate determined by the permeability of the wall and the osmotic pressure gradient across the wall, thereby producing a solution in compartment 93 that is dispensed through passageway 95 at a time controlled by device 91 over a prolonged period of time. The delivery of agent formulation from device 91 for homogenously blending with fluid in chamber 86, is controlled in this embodiment by device 91 and it is essentially independent of the rate of fluid flow through chamber 86. Device 91 maintains its physical and chemical integrity throughout its releasing history. In FIG. 4, the opened-section designated by the numbers 5-11, illustrates delivery devices that can be used for the present purpose in the formulation chamber. A description of the devices follows in FIG. 5 to FIG. 11 hereafter.

FIG. 5 depicts another device 96 for delivering an agent into a parenteral delivery system including an intravenously acceptable fluid that enters a formulation chamber. Device 96 is illustrated in opened-section and it comprises an inner mass transfer conductor 97, illustrated as a solid core and formed of a polymeric material such as cured polydimethylsiloxane, with agent 98 dispersed therethrough. Surrounding mass transfer conductor 97 is a release rate controlling membrane 99, preferably formed of a polymeric material, such as polyurethene. Both conductor 97 and membrane 99 are permeable to the passage of agent 98 by diffusion, that is, agent can dissolve in and diffuse through conductor 97 and membrane 99. However, the permeability of conductor 97 is greater than that of membrane 99, and membrane 99 thus acts as the rate controlling member for agent release from device 96. Device 96 maintains its physical and chemical integrity throughout the period of drug delivery. Delivery device 96 is disclosed in U.S. Pat. No. 3,845,480.

FIG. 6 illustrates a delivery device 100 designed for use in a formulation chamber for delivering an agent at a rate controlled by device 100 into a fluid that enters the chamber. Device 100 is seen in opened-section and it comprises a reservoir 101 formed of a liquid mass transfer conductor, such as a medical oil carrier, permeable to the passage of agent 102, such as the drug phenobarbital. Reservoir 101 is surrounded by a wall 103 formed of a release rate controlling material permeable to the passage of agent 102, such as a polyolefin. The rate of passage of agent 102 is lower through membrane 103 than the rate of passage through conductor 101, so that agent released by wall 103 is the agent release rate controlling step for releasing agent 102 from device 100. Device 100 maintains its physical and chemical integrity throughout its release history. Delivery device 100 is disclosed in U.S. Pat. No. 3,993,073, which patent is incorporated herein by reference.

FIG. 7 illustrates another device 104 for use in a formulation chamber for deliverying an agent into a liquid that enters a formulation chamber for forming a parenteral agent solution including an intravenously acceptable agent solution. Device 104 is seen in opened-section and it comprises a wall 105 surrounding a reservoir 106 containing agent 107. The reservoir is formed of a solid carrier permeable to the passage of agent, such as cured polydimethylsiloxane containing diazepam. Wall 105 is formed of a microporous material, for example a microporous polymer made by coprecipitation of a polycation and a polyanion. The release of agent 107 is controlled by device 104, which device 104 maintains its physical and chemical integrity during the period of time it is in a formulation chamber. Device 104 is disclosed in U.S. Pat. No. 3,993,072, which patent is incorporated herein by reference.

FIG. 8 is a view of a device 108 for delivering an agent into a medical fluid that enters the formulation chamber for forming in situ a parenteral or an intravenously acceptable agent formulation solution. Device 108 comprises a matrix 109 containing agent 110 distributed therein. Matrix 109 is formed from a polymeric material that is non-erodible and it is permeable to the passage of agent by diffusion for releasing agent over time, or it undergoes relaxation and releases agent 110 over time. The matrix can possess any shape such as rod, disc and the like that fits into a formulation chamber. The polymers include polyolefins such as polyethylene containing an agent such as muscle relaxants and the like. Materials useful for manufacturing the devices are disclosed in U.S. Pat. No. 3,921,636.

FIG. 9 is a view of a delivery device 111 for delivering a beneficial agent into a fluid that enters the formulation chamber. Device 111 is formed of a microporous polymeric matrix 112 containing agent 113 distributed therethrough. Matrix 112 is formed of a non-toxic, inert polymer, that is non-erodible and has a plurality of micropores for releasing agent 113 at a controlled rate to fluid entering the formulation chamber. Microporous materials useful for the present purpose are disclosed in U.S. Pat. Nos. 3,797,494 and 3,948,254.

FIG. 10 illustrates a delivery device 114 for delivering a beneficial agent into a medical fluid that enters a formulation chamber. Device 114 is seen in opened section and it comprises depots 115 of medication solute 115 dispersed in and surrounded substantially individually by a polymer wall 116 that is impermeable to the passage of medication solute and permeable to the passage of fluid that enters the formulation chamber. Medication solute 115 released at a controlled rate by fluid being imbibed through the polymer into the depots 115 to dissolve the solute in depot 115 and generate a hydrostatic pressure in the depots, which pressure is applied against the wall of the depot thereby forming apertures that release the medication at a controlled rate over time. Polymer 116 is non-erodible, and device 114 can be shaped as a matrix, rod, a disc, or like shapes. Procedures and materials useful for manufacturing the delivery system of FIG. 10 are described in U.S. Pat. No. 4,177,256.

FIG. 11 illustrates a device 117 useful for delivering a drug into a medically acceptable fluid passing through formulation chamber. Device 117 is seen in opened view and it comprises an exterior wall 118 formed of a semipermeable polymer permeable to fluid and substantially impermeable to the passage of drugs and solutes. A layer 119 of an osmotically effective solute, for example sodium chloride, is deposited on the inner surface of wall 118. Solute layer surrounds an inner container 120 formed of a flexible material that is impermeable to solute and drug. Container 120 has a passageway 121 for delivering a drug 122 into a fluid present in the formulation chamber. Device 117 dispenses drug by fluid permeating from the chamber through wall 118 to continuously dissolve drug solute 122 in a tendency towards osmotic equilibrium, thereby continuously increasing the volume between wall 118 and container 120. This increase causes container 120 to continuously collapse and dispense drug 122 from device 117 at a controlled rate through passageway 121 to fluid passing through the formulation chamber. Osmotically powered agent dispensing devices are disclosed in U.S. Pat. Nos. 3,760,984 and 3,995,631.

The delivery devices described in FIGS. 4 through 11 can contain various amounts of an agent, for example, from about 1 milligram to 20 grams, or more. The devices can release an agent at a rate of 10 nanograms per hour up to 3 grams per hour, or more, into a formulation chamber for forming an agent solution with the medical fluid that enters the chamber. The formulation chamber can optionally be considered as a cartridge, since they can be used in the secondary path once or replaced many times. That is, the cartridge can be removed after all the agent is delivered, or the cartridge can be replaced repeatedly each time after the device has delivered its agent. Thus, this mode of the invention can lead to intermediate or continuous therapy, in addition to the operations described in FIGS. 1 to 3.

FIG. 12 depicts another formulation chamber 125 that can be used in a parenteral delivery system as seen in FIGS. 1 to 3. FIG. 12 illustrates formulation chamber 125 that is light weight, disposable and indicated for use for patients requiring parenteral administration of a drug or an agent solution. In FIG. 12, chamber 125 comprises a body 126 of tube shape, and it has a pair of caps 127 and 128 that fit into body 126 for forming a closed chamber 125 for containing a fluid that enters chamber 125. Caps 127 and 128 are preferably made of self-sealing rubber through which a needle or a hollow spike can be inserted, or of rubber with a pre-drilled hole, not shown, covered by a latex disc through which communication can be made with the inside of chamber 125. Chamber 125 comprises wall 130 with a section removed for depicting internal lumen 131. Chamber 125 contains drug 129 that is soluble in parenterally acceptable fluids that enter chamber 125, and in a presently preferred embodiment chamber 125 houses a film 132 formed of a material operable for controlling the release of drug 129 in solution from chamber 125. Film 132, in a preferred embodiment, is formed of a release rate controlling microporous polymer such as polycarbonate, cellulose acetate, or ethylene-vinyl acetate copolymer and the like. The polymeric film according to the practice of the invention is used for governing the rate of drug solution release from chamber 125. Chamber 125 is illustrated with a film at its exit, and optionally it can have a film at its inlet. In an embodiment of the invention, the film can be placed vertically in the formulation chamber to the side of the inlet port confining the drug therein, with fluid passing through the film, forming a drug solution, and then returning to the fluid passing through the formulation chamber for eventual administration.

FIG. 13 illustrates a formulation chamber 133 that can be used in the therapeutic systems described in FIGS. 1 to 3. Chamber 133 comprises a wall 134 that surrounds and defines an internal lumen 135. A section of wall 134 is removed for illustrating the structure of chamber 133. Chamber 133 comprises a pair of closures 136 and 137 that fit over wall 134 for forming a closed chamber 133. The closures 136 and 137 each have a hollow member 138 and 139 that are preferably round for receiving a tube that can slide into, or slide over receiving members 138 and 139, thereby permitting chamber 133 to establish fluid communication with the parenteral therapeutic system. FIG. 13 further illustrates agent 140 in particle form, a release rate controlling polymeric film 141 and a filter 142. Filter 142 is a conventional filter with a pore size of 0.1 micron to 5 micron, and more preferably 0.22 micron or 0.45 micron, for removing bacteria and unwanted matter from a flowing solution.

The parenteral delivery system comprising the primary path and the secondary path with the agent formulation chamber in the secondary path can be used for the administration of many beneficial agents especially, where it is desirable to administer by infusion, and more particularly via the intravenous, intra-arterial, intraperitioneal or subcutaneous routes. For example, the delivery system can be used in one presently preferred embodiment, in intravenous fluid replacement, such as administering plasma or saline and simultaneously or intermittently administering a therapeutically effective amount of drug therewith; in another embodiment as a method in intravenous electrolyte-balance replacement, such as supplying sodium, potassium or chloride ions with drug administered therewith to a patient in need of electrolyte restoration and an intravenous drug; and in a method of intravenous nutrition, such as supplying dextrose and concomitantly administering or periodically administering a parenterally administrable drug to a patient in need of such therapies.

The novel and useful invention provides a system and method for obtaining the precise control of agent administration to a recipient. While there has been described and pointed out features of the invention as applied to presently preferred embodiments, those skilled in the art will appreciate that various modifications, changes, additions and omissions in the invention illustrated and described can be made without departing from the spirit of the invention.

We claim:

1. A parenteral delivery set for administering a beneficial agent formulation to a warm-blooded animal, the delivery set comprising:

(a) a primary tube for the flow of a parenterally acceptable fluid therethrough;
(b) a secondary tube for the flow of a parenterally acceptable fluid therethrough;
(c) a formulation chamber having means for establishing communication with the secondary tube, the formulation chamber comprising:
 (1) a wall that surrounds an internal lumen;
 (2) an inlet in the wall for letting a parenterally acceptable fluid enter the formulation chamber;
 (3) a beneficial agent osmotic delivery device in the formulation chamber, the delivery device comprising:
  (i) a wall formed of a semipermeable composition that surrounds and forms a compartment,
  (ii) a beneficial agent in the compartment, and
  (iii) a passageway in the wall of the delivery device connecting the compartment with the formulation chamber;
 (4) an outlet in the wall for letting an agent formulation leave the formulation chamber;
(d) a common tube having means for communicating with the primary tube for receiving parenterally acceptable fluid from the primary tube, and for communicating with the secondary tube for receiving parenterally administrable agent formulation from the secondary tube.

2. The parenteral delivery set for administering the beneficial agent formulation according to claim 1, wherein the formulation chamber is replaced each time the device has delivered the beneficial agent.

3. The parenteral delivery set for administering the beneficial agent formulation according to claim 1, wherein the beneficial agent is an intravenously administrable drug.

* * * * *